(12) United States Patent
Stelzer et al.

(10) Patent No.: US 6,437,513 B1
(45) Date of Patent: Aug. 20, 2002

(54) IONIZATION CHAMBER FOR ION BEAMS AND METHOD FOR MONITORING THE INTENSITY OF AN ION BEAM

(75) Inventors: Herbert Stelzer; Bernd Voss, both of Darmstadt (DE)

(73) Assignee: Gesellschaft fuer Schwerionenforschung mbH, Darmstadt (DE)

( * ) Notice: Subject to any disclaimer, the term of this patent is extended or adjusted under 35 U.S.C. 154(b) by 0 days.

(21) Appl. No.: 09/890,747
(22) PCT Filed: Feb. 18, 2000
(86) PCT No.: PCT/EP00/01390
§ 371 (c)(1), (2), (4) Date: Nov. 15, 2001
(87) PCT Pub. No.: WO00/49639
PCT Pub. Date: Aug. 24, 2000

(30) Foreign Application Priority Data

Feb. 19, 1999 (DE) .......................................... 199 07 207

(51) Int. Cl.⁷ .................................................. H01J 7/24
(52) U.S. Cl. ............... 315/111.81; 250/283; 250/385.1; 250/492.3
(58) Field of Search ........................ 315/111.81, 111.01; 250/283, 385.1, 389, 395, 423 R, 424, 489, 492.3

(56) References Cited

U.S. PATENT DOCUMENTS 3,601,609 A * 8/1971 Yauger ........................ 250/308
5,120,967 A * 6/1992 Cappelli et al. ............. 250/374
5,326,976 A * 7/1994 Kikuchi .................... 250/385.1
5,508,526 A * 4/1996 Labb ........................... 250/374

FOREIGN PATENT DOCUMENTS

DE 3411335 A1 * 10/1985

* cited by examiner

Primary Examiner—Don Wong
Assistant Examiner—Thuy Vinh Tran
(74) Attorney, Agent, or Firm—Frommer Lawrence & Haug; Ronald R. Santucci (57) ABSTRACT

The invention relates to an ionization chamber for ion beams and to a method of monitoring the intensity of an ion therapy beam by way of such an ionization chamber. For that purpose, the ionization chamber includes a chamber housing, a beam inlet window and a beam outlet window, a chamber volume filled with counting gas, a high-voltage anode and a high-voltage cathode, wherein the ionization chamber is constructed flat and sandwich-like from plate-shaped large-surface-area structures of the above-mentioned components, which are aligned orthogonally relative to the axis of the ion beam, and a centrally arranged large-surface-area orthogonally aligned plate-shaped counting anode is surrounded on both sides by a large-surface-area plate-shaped high-voltage cathode consisting of two parallel cathode plates, and the chamber housing consists of a housing frame, which frames a square ionization chamber volume, and on which frame the beam inlet window and the beam outlet window are mounted gas-impermeably.

16 Claims, 4 Drawing Sheets

IONIZATION CHAMBER FOR ION BEAMS AND METHOD FOR MONITORING THE INTENSITY OF AN ION BEAM

TECHNICAL FIELD

The invention relates to an ionisation chamber for ion beams and to a method of monitoring the intensity of an ion beam according to the preamble of claims 1 and 16.

BACKGROUND OF THE INVENTION

Such ionisation chambers are also known in the prior art as ion counting tubes. The chamber housing is customarily made from a tube, with one of the two end portions of the tube serving as the beam inlet window and the other end of the tube serving as the beam outlet window. The tube is filled with a counting gas under reduced pressure and has a cylindrical high-voltage cathode that lies coaxially in the counting tube, insulated from the tube wall. Located in the centre of the tube is a cylindrical high-voltage anode which is insulated from the high-voltage cathode and the surrounding tube. In order to operate the ionisation chamber, a voltage is applied between the high-voltage cathode and the high-voltage anode and the current between the cathode and anode is measured. If charged particles, such as ions, are passed through the ionisation chamber or are captured by the ionisation chamber, the current between the cathode and the anode increases in dependence upon the number of ions that pass through the ionisation chamber. More complex cylindrical ionisation chambers have a large number of axially aligned anodes in order, for example, to measure the path of a charged particle or ion through a tubular ionisation chamber by means of anodes distributed axially over the cross-section.

A disadvantage of such cylindrical ionisation chambers is their large axial dimension and the relatively complex construction of the counting anodes. Moreover, the space required by such ionisation chambers in the direction of the diffusion of a beam is relatively large. The space available at the beam outlet in a treatment room in front of patients is, however, very limited. Moreover, with therapy systems in which an ion beam is scanned over the entire extent of a tumour tissue, there must be available an ionisation chamber of hitherto unknown dimensions in terms of breadth and length. Generally, all the measurements in the beam must be carried out in front of the patient in the transmission mode. It is imperative to avoid impairment of the quality of the beam, for example as a result of projectile fragmentation and angular scatter of the beam particles.

SUMMARY OF THE INVENTION

The problem underlying the invention is accordingly to provide an ionisation chamber for ion beams and a method of monitoring the intensity of an ion therapy beam that overcomes the disadvantages of existing ionisation chambers, is suitable for monitoring and controlling patient irradiation in the context of tumour therapy with heavy ions that are concentrated with high energy into a pencil beam, in which the dimensions of the detector in the direction of the beam are small, that enables a high level of safety to be achieved, especially in respect of plasma and spark formation, and can be used in the field of medicine.

For that purpose, the ionisation chamber for ion beams consists of a chamber housing, a beam inlet window and a beam outlet window, a chamber volume filled with counting gas and a high-voltage anode and a high-voltage cathode. The ionisation chamber is constructed flat and sandwich-like from plate-shaped large-surface-area structures of those components, which are aligned orthogonally relative to the axis of the ion beam. A centrally arranged large-surface-area orthogonally aligned plate-shaped counting anode is surrounded on both sides by a large-surface-area plate-shaped high-voltage cathode consisting of two parallel cathode plates. The chamber housing consists of a housing frame which frames a virtually square ionisation chamber volume, and on which frame the beam inlet window and beam outlet window are mounted gas-impermeably. Such a device has the advantage of being easier to maintain since the plate-shaped construction can be removed from the housing frame and replaced by simply dismantling or removing different plate structures. The plates can be replaced easily and suitable numbers thereof can be held in stock. The plate-shaped structure also enables mass production of spare parts and finished ionisation chambers.

In a preferred embodiment of the invention, the counting gas is a gas mixture of argon or krypton and carbon dioxide, preferably having a gas volume mixing ratio of 4:1, which is adapted to the energy and intensity of the ion beam, and is introduced into the ionisation chamber. A counting gas of such composition has the advantage, compared with customary air-filled cylindrical ionisation chambers, that the measurements are easier to reproduce since in this case air humidity does not influence the sensitivity of the ionisation chamber. Such a counting gas ensures a good signal/noise ratio and makes available a high dynamic range in the particle rates. With the preferred counting gas, sufficient dielectric strength is also ensured.

Such a counting gas is preferably of the highest purity since the signal sensitivity, especially in its amplitude and waveform, is impaired by impurities. Moreover, inside the chamber volume there are preferably used for the individual plate elements and other supporting and insulating elements as well as for auxiliary units and sensors materials that do not release gases, or elements and components that do release gases are cast in epoxy resin.

In a further preferred embodiment, the ionisation chamber has sensors that are mounted in the housing frame in through openings that are gas-impermeably sealed and that measure the counting gas pressure and the counting gas temperature. The ionisation chamber is operated with slightly elevated pressure compared with the ambient air, which advantageously makes penetration of extraneous gases more difficult. For that purpose, the extent of the gas reflux from the chambers is monitored by a sensor system in the counting gas outlet region or in the outlet. By measuring gas pressure and gas temperature, it is advantageously possible to monitor the gas density and, if necessary, keep it constant, the gas density being used directly in the determination of the ion beam particle number.

The beam inlet window and the beam outlet window, which are substantially square, preferably consist of radiation-resistant non-polarisable plastics films. These are secured to metal plate-shaped frames, which in turn seal off the ionisation chamber volume gas-impermeably from the beam inlet window and from the beam outlet window by means of O-ring seals in the housing frame. That gas-impermeable construction keeps impurities away from the counting gas and gas exchange of the chamber volume with the environment by diffusion is minimised even when the ionisation chambers are not in operation.

The beam inlet window and the beam outlet window preferably comprise polyimide or polyester films, which has the advantage that exclusively radiation-resistant and non-polarisable materials are exposed to the ion beam, so minimising the effect on the ion beam and the ion beam intensity.

In a further preferred embodiment of the invention, the beam inlet window and the beam outlet window are metallised on the side facing the ionisation chamber volume. Such metallisation of the beam inlet window and the beam outlet window prevents the windows from becoming charged and thus prevents falsification of the measurement values, since charges can be conducted away to the ionisation chamber housing directly by way of the metallisation of the windows and by way of the window frames. The ionisation chamber housing is thus advantageously earthed.

Such metallisation can be achieved by aluminising or nickel-plating one of the sides of the beam inlet window or beam outlet window. Such aluminised films have a conductive layer in order to avoid high electrical field densities as trigger points for gaseous discharges, so that the occurrence of gaseous discharges is minimised. Moreover, metallised films form a smooth surface which also serves to prevent high electrical field densities at trigger points for gaseous discharges.

The large-surface-area plate-shaped counting anode and the large-surface-area plate-shaped high-voltage cathode preferably consist of mesh mounted in a frame which is supported against the housing frame in an electrically insulating manner. In the process, electrically insulating spacing elements define the spacing between the counting anode and the high-voltage electrode. The use of meshes instead of films for the anode and cathode has the advantage that it is possible to operate with relatively large mechanical pre-stressing for the detector planes of mesh material. The uniformity of the signal across the site and across the extent of the detector surface of the ionisation chamber is thus improved, which has an advantageous effect in particular in the case of the relatively large chamber cross-sections in the edge regions of the active volume of the chambers.

Compared with large-surface-area films as counting anode surfaces or as cathode surfaces, meshes have the advantage that there is less sagging, in particular when high voltage is applied, because of their higher pre-stressing capacity. Such sagging is caused by mutual electrostatic attraction of the films or mesh electrodes mounted parallel with one another. When meshes are used, however, the spacing of the electrodes from one another, especially in the centre, remains relatively constant so that the field densities can advantageously be kept locally constant.

Instead of using metal fibre mesh, it is preferable to use for the large-surface-area plate-shaped counting anode and the large-surface-area plate-shaped high-voltage cathode mesh made from metal-coated plastics fibres. Such mesh made from composite fibres of plastics and metal coating has the advantage that it is lighter and can be loaded with relatively high pre-stressing and it has a low nuclear charge number for the carrier filaments. The electrode function is provided by the metal coating and a capacity to bear a high mechanical load is achieved as a result of the plastics core of the fibres, that capacity to bear a high mechanical load in turn being a precondition for high mechanical pre-stressing of the high-voltage plate electrodes.

The large-surface-area plate-shaped high-voltage electrode and the large-surface-area plate-shaped counting anode are preferably made of nickel-coated plastics mesh or nickel-coated polyester mesh. That composite material has the advantage not only that its plastics part consists of radiation-resistant and non-polarised materials but also that it provides a smooth surface, which allows high electrical field densities without triggering gaseous discharges.

In a preferred embodiment, the counting gas is supplied into the region of the ionisation chamber volume that is lowermost with respect to gravity, and is discharged in the uppermost region. For that purpose, the housing frame of the ionisation chamber has a counting gas inlet opening and a counting gas outlet opening. By means of that preferred embodiment, advantageously a laminar flow of counting gas through the ionisation chamber can be provided by way of the counting gas inlet opening and the counting gas outlet opening. Inside the chamber, the counting gas is preferably guided through stainless steel tubes having variable outlet and inlet holes.

A gas flow sensor is preferably arranged outside the ionisation chamber volume in order to monitor the throughflow of counting gas, so as to keep the chamber volume as small as possible. In addition to simply monitoring the counting gas throughflow, it is also possible to regulate the counting gas with the aid of such gas flow sensors in conjunction with pressure and temperature sensors.

Preferably the central counting anode and the high-voltage cathode in question are arranged relative to one another at a spacing of from 3 to 13 mm, especially 5 mm, and can be operated at high voltages of more than 1500 V. For that purpose, the plate-shaped electrodes must be insulated from one another by insulating parts, such as the frame, the spacing pieces, and adhesion and casting compositions, those insulating parts having high volume and surface electrical resistance values of, respectively, from $10^{12}$ to $10^{14}$ $\Omega/cm^3$ and from $10^{16}$ to $10^{18}$ $\Omega/cm$. This advantageously reduces leakage or tracking currents, which would otherwise falsify the measurement and impair the sensitivity of the system as a whole.

In a further preferred embodiment, the ionisation chamber is developed to form an ionisation chamber system for ion beams. For that purpose, a plurality of ionisation chambers of the type according to the invention are arranged behind one another in the direction of the beam and are used to form a system for monitoring the intensity of a heavy ion therapy beam. Owing to the high safety standards that must be met in the case of therapy beams, at least two ionisation chambers are arranged in tandem behind one another in the direction of the ionisation beam in order to monitor the individual dose of a volume element and the layer dose of a scanned layer and are used for the independent monitoring of the total dose of a treatment cycle independently of the ionisation chamber for monitoring the individual dose and the layer dose.

Owing to the flat construction of a single ionisation chamber, that ionisation chamber system has the advantage that in the direction of the beam it requires very little space whereas, transverse to the beam, it extends over the full scanning surface. Since using a raster scanner the ion beam scans the target volume by volume and by layer, advantageously the individual dose per volume element is monitored by a first ionisation chamber in the ionisation chamber system and the layer dose is monitored by adding together all the individual doses of a scanned layer. A second ionisation chamber independent of the first ionisation chamber can advantageously monitor the total dose of a treatment cycle. Instead of the preferred two ionisation chambers, it is also possible to connect three ionisation chambers behind one another, which then monitor the individual dose of a volume element, the layer dose of a scanned layer and the total dose of a treatment cycle, respectively.

In a further preferred embodiment, the first and second ionisation chambers monitor the pixel dose and the layer dose with redundancy. The second ionisation chamber thus monitors the first ionisation chamber. A third ionisation chamber is connected to different electronics and monitors integral values, such as when the dose falls short of a maximum dose in the treatment plan.

In order to increase safety, the individual dose for a volume element can be measured in the first and second ionisation chambers of an ionisation chamber system comprising three ionisation chambers, and the results of the first and second ionisation chambers can be compared so that if the measured data from the first and second ionisation chambers depart from a predetermined tolerance range, a rapid switch-off of the ion therapy system can be triggered. Such a comparison increases the operating safety of the first and second ionisation chambers. Similarly, the layer dose of a layer to be irradiated (also called irradiation layer) can be measured and compared by the second and third ionisation chambers of the ionisation chamber system comprising three ionisation chambers so that if the measured results from the second and third ionisation chambers exceed a predetermined tolerance range a safety switch-off of the ion beam therapy system can be triggered.

The method of monitoring the intensity of a heavy ion beam by means of ionisation chambers or by means of the ionisation chamber system comprises the following method steps:

a) measurement of the intensity dose of an irradiation volume element of a planned irradiation raster for an irradiation layer by means of a first ionisation chamber;

b) monitoring of the measured value of the intensity dose of an irradiation volume element by a second ionisation chamber arranged in tandem behind the first ionisation chamber;

c) comparison of the measured value of the first ionisation chamber with the monitoring value of the second ionisation chamber and clearance for the irradiation of the next irradiation volume element of a planned irradiation raster of an irradiation layer when the two irradiation intensity values match within a predetermined desired value range;

d) emergency switch-off of the radiation treatment when the predetermined desired value range is exceeded and readjustment of the intensity when it falls short of the predetermined desired value range;

e) repetition of the steps for the subsequent planned treatment layers until the volume of tissue to be irradiated has been fully scanned;

f) integration of all the measured radiation doses of the monitoring values in a third ionisation chamber, which is arranged in tandem behind the first and second ionisation chambers, in order to monitor the total radiation to which a volume of tissue is subjected during a treatment cycle.

By means of that method, advantageously the number of particles or heavy ions extracted per second from an accelerator and used as an ion beam for tumour therapy is measured. The number of particles is subject to large temporal variations and must accordingly be measured in real time during irradiation directly by those ionisation chambers. The current measured at the outlet of the chambers is proportional to the ion beam current when the particle energy remains constant. In typical beam currents of the accelerator, the currents coming from the ionisation chambers are in the region of $\mu A$.

The response speed of the ionisation chambers is limited by the drift time of the ionised counting gas molecules in the ionisation chamber and has a delay constant in the order of magnitude of about $10\,\mu s$. Measuring electronics convert the current from the ionisation chamber to a proportional frequency of pulses. For that purpose, voltage signals are produced from the current signal and pulses are formed from the voltage signal by means of amplitude-frequency conversion, the frequency of which pulses is proportional to the voltage. Accordingly, a pulse corresponds to a specific charge produced in the ionisation chamber, the charge in turn being produced by a specific particle number of the ion beam. The number of pulses produced is thus proportional to the number of ions flowing through the ionisation chamber.

Accordingly, using the method it is advantageously possible to monitor the intensity dose of an irradiation volume element, the intensity dose of a total irradiation layer and finally the intensity dose of a whole treatment cycle. The method also comprises safety-relevant redundancy, in that in practice both the intensity dose of an irradiation volume element and the intensity dose of an irradiation layer are measured in two ionisation chambers and the measured values are compared directly with one another, so that in the event of unacceptable deviations an emergency switch-off of the system can be triggered. It is also possible to add to each of the three ionisation chambers summation electronics so that all three ionisation chambers can monitor the total dose of a radiation cycle of an irradiation volume simultaneously and in parallel. Thus, by means of the ionisation chambers according to the invention and in particular by means of the ionisation chamber system according to the invention comprising three ion beam chambers arranged behind one another in the direction of the ion beam, it is possible to achieve the greatest possible safety and reliability during the irradiation of a tumour volume with ion beams.

In a preferred embodiment of the method, the order in which the method steps are carried out is adapted optimally to the planned treatment cycle in question. In a preferred further development of the method, the monitoring function of the first and second ionisation chambers is provided by a single ionisation chamber. Whilst this reduces the redundancy of the method, the space required for the detector systems in the form of ionisation chambers is advantageously reduced.

BRIEF DESCRIPTION OF THE DRAWINGS

Further advantages, features and possible applications of the invention will now be explained in greater detail with reference to embodiments and referring to the attached drawings.

DETAILED DESCRIPTION OF THE INVENTION

Figure 1:
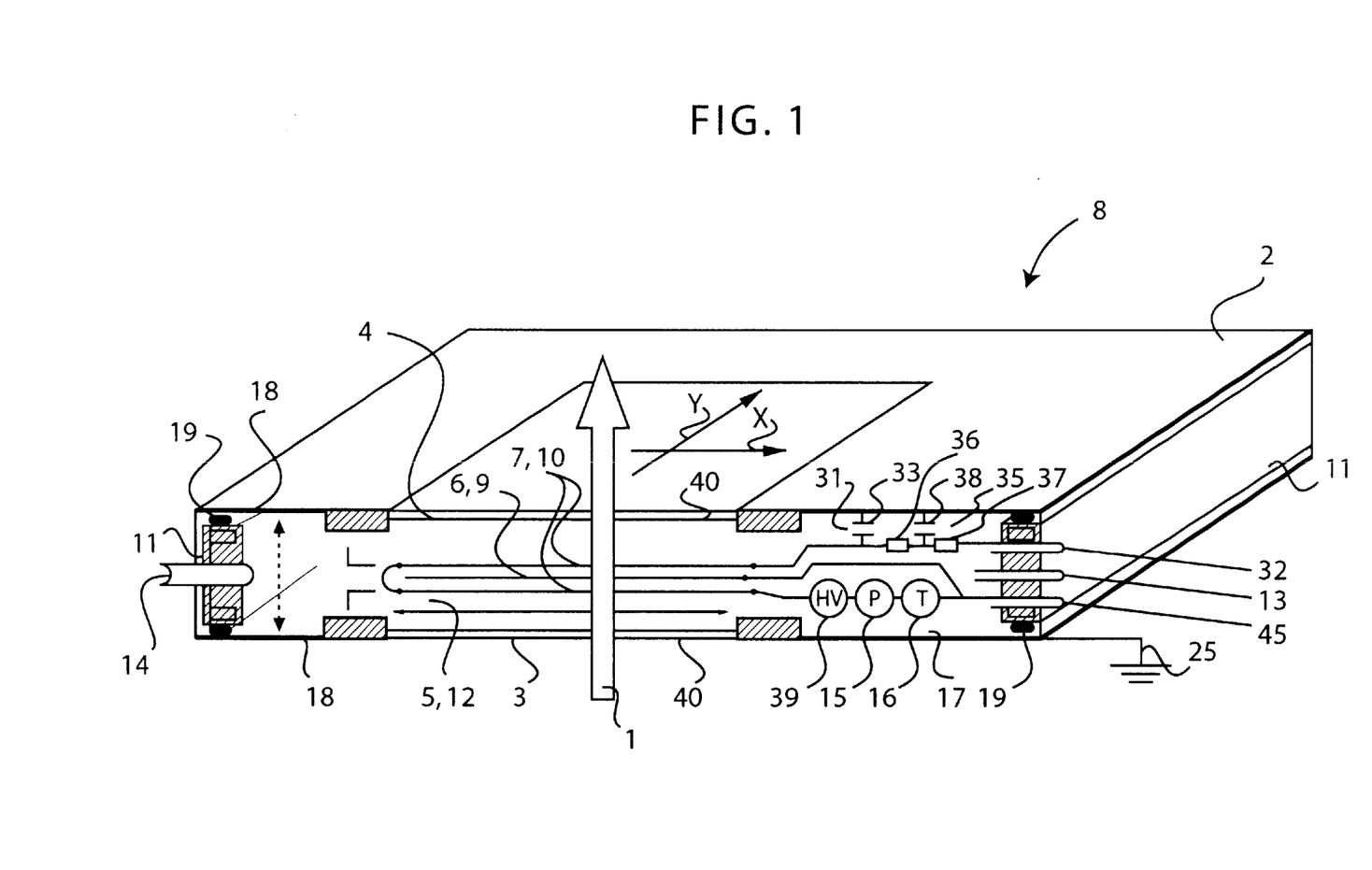
FIG. 1 is a perspective view of the basic structure of a preferred embodiment of the ionisation chamber according to the invention.

FIG. 1 is a perspective view of the basic structure of a preferred embodiment of the ionisation chamber 8 according to the invention. The parallel-plate ionisation chamber 8 shown here serves to monitor and control patient irradiation in the context of tumour therapy with heavy ions. It consists essentially of a chamber housing 2, a beam inlet window 3 and a beam outlet window 4, a chamber volume 5 filled with counting gas, a high-voltage anode 6 and a high-voltage cathode 7 which is arranged on both sides of the high-voltage anode 6. The ionisation chamber is intended for the field of medicine and is constructed sandwich-like and flat from plate-shaped large-surface-area structures of the individual components, which are aligned orthogonally relative to the ion beam 1. The components include a centrally arranged large-surface-area orthogonally aligned plate-shaped counting anode 9, which is surrounded on both sides by a large-surface-area plate-shaped high-voltage cathode 7 consisting of two parallel cathode plates 10. The chamber housing 2 consists substantially of a housing frame 11, which frames a square ionisation chamber volume 12, and on which frame the beam inlet window 3 and the beam outlet window 4 are mounted gas-impermeably. In the field of medicine, such an ionisation chamber 8 must have a high level of safety, high reliability and must be very easy to maintain. For that reason the present embodiment meets the following outline conditions and requirements, the following irradiation parameters being determining for this embodiment:

| Type of beam: | protons, carbon oxygen | $^{12}C^{6+}$ (preferably) |
|---|---|---|
| energy: | 80 . . . 430 MeV/u | in 253 steps |
| focus: | 4 . . . 10 mm | in 4 to 7 steps |
| intensity: | $2 \times 10^6 - 4 \times 10^{10}$ particles/extraction | in 10 to 20 steps |
| Geometry of irradiation: | $200 \times 200$ mm$^2$ | in the isocentre plane |
| Characteristic times: | 1–10 s | ion beam extraction time |
| | 2–4 s | beam pause |
| | $\geq 1000$ $\mu$s | per irradiation point of a volume element |
| | <1000 $\mu$s | for interruption of the beam |
| | 100 $\mu$s–250 $\mu$s | per position measurement |
| | 10 $\mu$s–15 $\mu$s | per intensity measurement |

During an extraction phase of about 2 s, the carbon ions extracted from an ion accelerator system, such as a heavy ion synchrotron, fly through the ionisation chamber and on impact with the counting gas release some of their kinetic energy to that gas. Some of that energy results in the production of electron-ion pairs. The number of electron-ion pairs is proportional to the number of ions of the ion current that have flown through. The charges so produced in the active ionisation chamber volume 12 are separated in an applied electrical field and recorded and evaluated by the downstream measuring electronics. For that purpose, the active region consists only of the spaces between the electrodes. Only charges produced therein are detected and measured. The charges produced in the areas between electrodes and chamber windows are drawn off to the high-voltage planes 7 and/or to the windows 3, 4 and thus do not contribute to the signal formation. They are excluded from the measurement since the field inhomogeneities caused by the geometry in those areas do not permit any representative intensity measurements.

Figure 5:
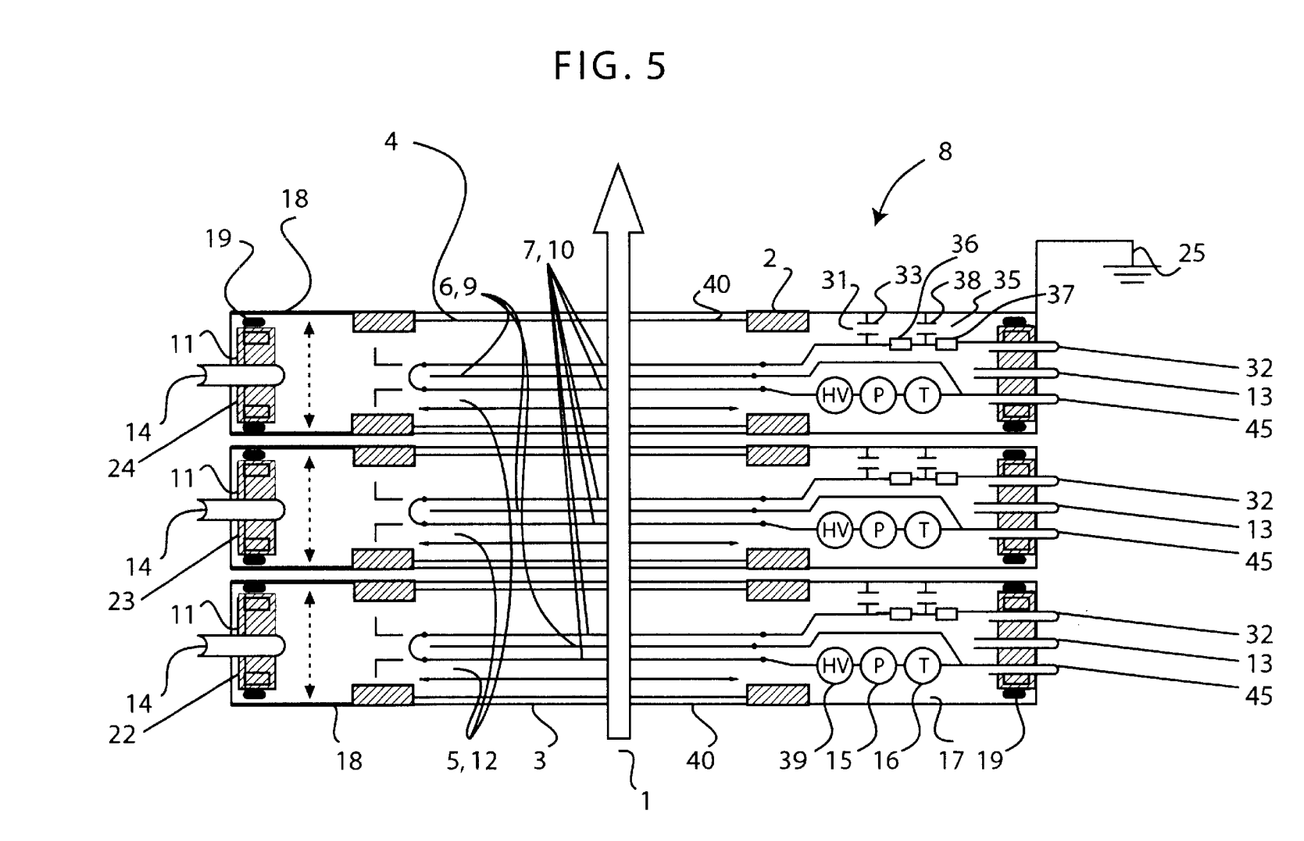
FIG. 5 is a cross-section through the basic structure of an ionisation chamber system.

In an ionisation chamber system 30 of three ionisation chambers 22, 23 and 24, the evaluation takes place in two of those ionisation chambers 22 and 23 every 12 its. By comparing those values with the desired values determined previously in the context of radiation planning, that information is used to regulate the scanning speed of a raster scanner at the site of treatment. The third ionisation chamber 24, shown in FIG. 5, is of the same type of construction and is used to determine the total particle number for an isoenergy step, that is to say for an irradiation layer, and for the total radiation dose of a radiation cycle for a tumour volume. By monitoring those integral values, namely the irradiation layer and the irradiation volume, further safety is provided for scanning the tumour volume in a patient.

An area of about 190×190 mm$^2$ is covered by the scanning apparatus, a scanner, at the site of the ionisation chambers 22, 23, 24. Accordingly, the ionisation chambers 22, 23, 24 of that preferred embodiment have a large active cross-section with an aperture width for the beam inlet window 3 and the beam outlet window 4 of 210×210 mm$^2$. By using materials having a relatively high modulus of elasticity, it is advantageously possible to overcome the difficulties of such dimensions, especially in the structure of the counter.

Each ionisation chamber 8, 22, 23, 24 is in the form of a Faraday cage, advantageously so avoiding electromagnetic interference. When cabling the plate-shaped large-surface-area high-voltage electrodes 6 and 7, earth loops outside the ionisation chambers are avoided structurally in order to minimise electromagnetic interference.

The housing frame 11 of the ionisation chamber 8 in that embodiment is made from a solid aluminium material, the frames of the windows 18 are made from stainless steel and the window films of the beam inlet window 3 and the beam outlet window 4 are made of metallised plastics films that are about 25 m thick, which are attached by adhesion in the frame 18 of the windows so as to be electrically conductive. All conductive parts that do not carry electrical potentials are earthed centrally by the earth connection 25. Where possible, for materials through which the ion beam 1 must pass in the active ionisation chamber volume 12 there are used materials having low nuclear charge numbers, preferably plastics comprising hydrogen and carbon that are as thin as possible and thus their mass present in the actual path of the ion beam is as small as possible. This has the advantage that impairment of the beam quality, such as by projectile fragmentation and angular scatter of the beam particles, is minimised by those materials. Moreover, only radiation-resistant and non-polarisable substances are used for such materials in that embodiment.

Figure 2:
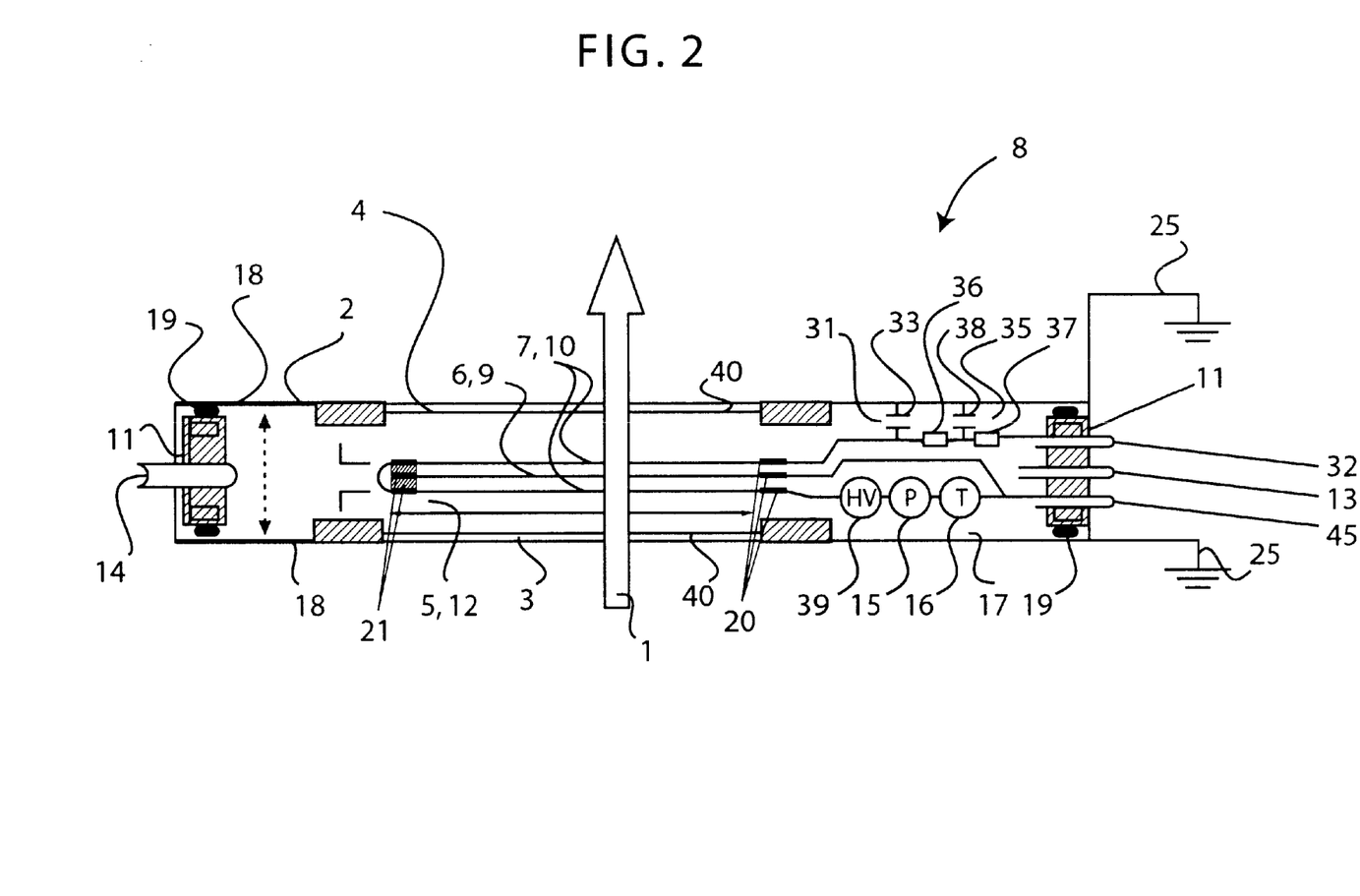
FIG. 2 is a diagrammatic cross-section through the preferred embodiment according to FIG. 1.

The insulating parts, which are shown in FIG. 2, such as the frame 20 of the counting anode 6 and of the high-voltage cathode 7 and the spacing elements between those frames as well as the adhesion and casting compositions have a volume and surface resistance value of, respectively, from $10^{12}$ to $10^{14}$ $\Omega$/cm$^3$ and from $10^{16}$ to $10^{18}$ $\Omega$/cm. Those high surface and volume resistances have the advantage of reducing dark currents, which would falsify the measurements and impair the sensitivity of the system as a whole.

Conductive parts in that embodiment are provided with smooth surfaces, advantageously so avoiding high electrical field densities as trigger points for gaseous discharges. The films for the beam inlet window 3 and the beam outlet window 4 are accordingly aluminised and the high-voltage anode 6 or counting anode 9 and the high-voltage cathode 7 or the high-voltage cathode plates 10 are accordingly manufactured from mesh having a high mesh number and are coated with nickel, in order here also to achieve relatively smooth surfaces.

FIG. 2 is a diagrammatic cross-section of the preferred embodiment according to FIG. 1. According to the planar irradiation geometry, the ionisation chamber 8, as shown in the perspective view of FIG. 1, is in the form of parallel-plate ionisation chambers 8, 22, 23, 24. The ionisation chamber 8, as shown in FIG. 2, is symmetrical in the construction of its counting anode 9 between two high-voltage cathode plates 10 with a spacing of 5 mm in each case in the direction of the beam. That advantageously provides an exact definition of the active volume. Furthermore, with the same drift time of the electron-ion pairs, the signal and thus also the signal/noise ratio is advantageously twice as great as in an asymmetrical construction of, for example, two films. The non-active and thus dead zone of the ionisation chamber is from 8 to 22 mm in the direction of the beam so that in the direction of the beam the total dimension of the ionisation chamber 8 in that embodiment is from 18 to 32 mm.

The counting anode 9, spacing elements 21 and high-voltage cathode planes 10 are aligned with one another in order to obtain a precise definition of the active volume 12. For that purpose, those planes are arranged parallel to each other and perpendicular to the ion beam 1 by means of low-tolerance common suspension points of the planes in the direction of the beam using corresponding spacing pieces.

Unavoidable leakage currents between high-voltage-carrying parts, such as the cathode plates 10 and the counting anode 9, are kept away from the signal electrodes and conducted away by earthed protective electrodes.

To produce the chamber planes, such as the cathode plates 10 and the counting anode 9, in that embodiment a nickel-coated polyester mesh was used. The chamber planes, especially the chamber electrodes, thus have high resistance to large ionisation densities as a result of high particle densities and high particle rates in the ion beam 1 during extraction from a synchrotron.

The nickel-coated polyester mesh of the electrodes preferably consists of a screen print mesh having a fibre thickness of 38 $\mu$m, a fibre spacing of 54 $\mu$m and an open surface area of 34.45%. The fibre thickness is composed of a 36 $\mu$m thick polyester core and a 1 $\mu$m thick nickel coating. The average thickness of the nickel-coated polyester mesh is 62 $\mu$m and the maximum equivalent range of the carbon beam particles in that mesh is about 100 $\mu$m.

Both the use of mesh per se and the selection of polyester as carrier and nickel as coating material offer advantages that are described hereinafter.

On the one hand, the use of mesh planes rather than films has the following advantages:
  a) the construction of the detector planes involved in the signal formation from mesh material permits greater mechanical pre-stressing of more than 10 Ncm compared with film planes.
  b) the uniformity of the signal across the site is thus improved, which has a positive effect in particular in the case of the relatively large chamber cross-sections in the edge regions of the active volume of the ionisation chamber 8.

Figure 3:
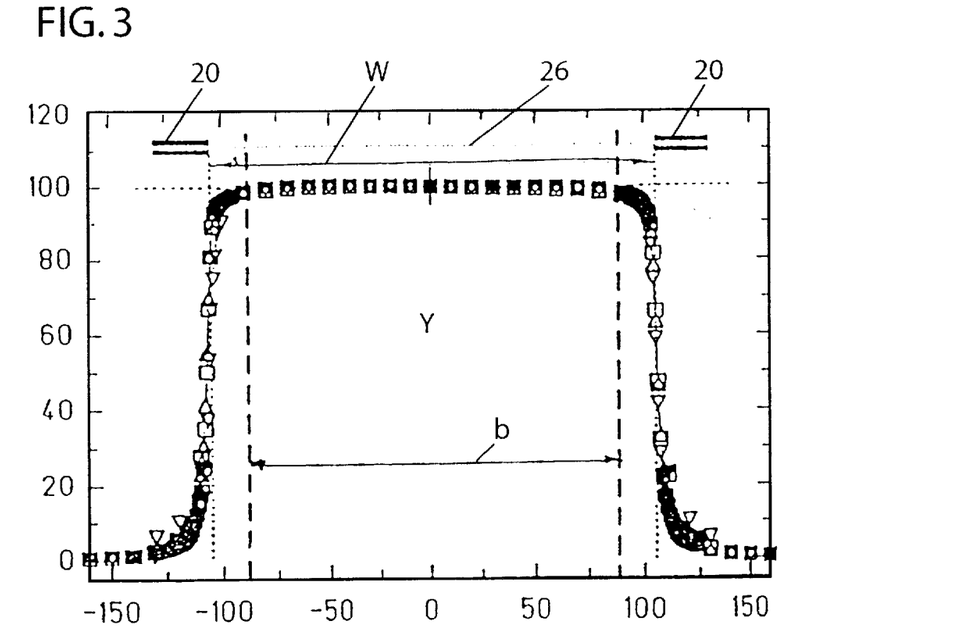
FIG. 3 shows, in the Y-direction, the homogeneity of the local response behaviour of an embodiment of the ionisation chamber according to the invention.
Figure 4:
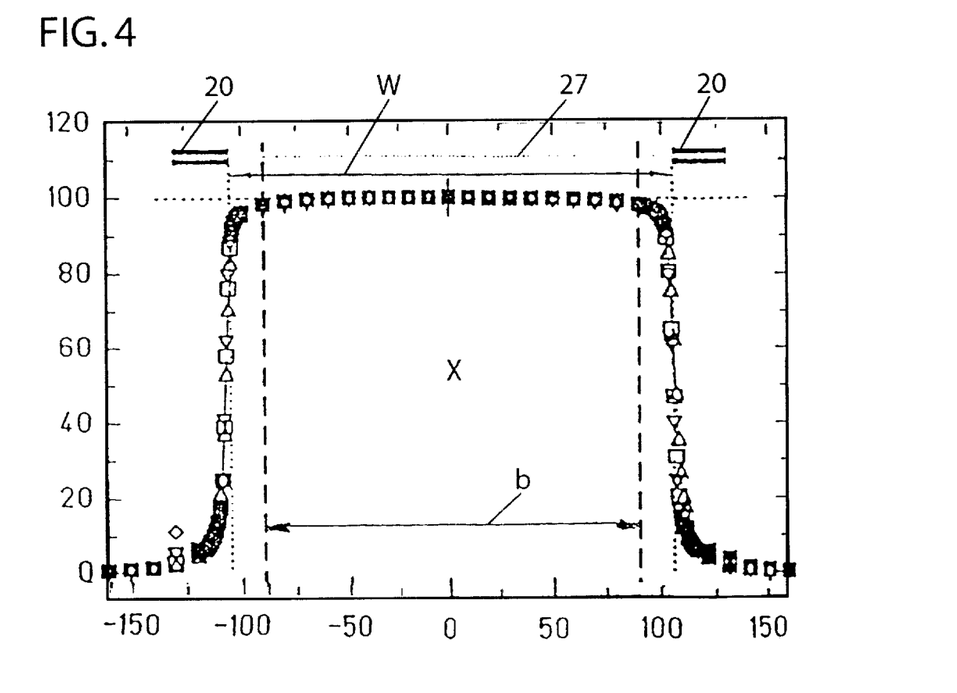
FIG. 4 shows, in the X-direction, the homogeneity of the response behaviour of an embodiment of the ionisation chamber according to the invention.

FIG. 3 shows, in the Y-direction, the homogeneity of the local response behaviour of an embodiment of the ionisation chamber 8 according to the invention, and FIG. 4 shows, in the X-direction, the homogeneity of the local response behaviour of an embodiment of the ionisation chamber 8 according to the invention.

In FIGS. 3 and 4, the spacing in mm from the centre of the ionisation chamber 8 is plotted along the abscissa and the relative signal amplitude obtained is shown in % along the ordinate. The dotted line in the upper region of FIGS. 3 and 4 symbolises the nickel-coated mesh of the electrodes 26 and 27, which is mounted in the frame 20 which has an internal width w of 210 mm. It can clearly be seen that, over an active volume breadth b of 190 mm, the local response behaviour of the chamber, that is the signal, is extremely homogeneous, and falls off steeply only towards the edge, that is say towards the mounting frames 20 of the meshes 26 and 27. That uniformity and homogeneity of the signal is especially noticeable when the high voltage applied is large, at which voltage the planes of ionisation chambers comprising films already have a clear tendency to sag as a result of mutual electrostatic attraction. As a result of the higher mechanical pre-stressing of the meshes in their frames 20, the sagging of such electrodes is less than in the case of electrodes made from films. This is especially the case because, compared with film electrodes, the spacing of the electrodes from one another in the centre is hardly reduced at all and thus in mesh electrodes the field densities remain locally constant.

Triggering of sparks especially at the point of greatest sagging in the centre of the ionisation chamber 8 does not occur until greater high-voltages, at which voltages the metallisation in film chambers would be destroyed in a very short space of time.

Comparatively this has the advantage of higher maximum operating voltages of about 1900 V for mesh chambers compared with about 1000 V for mesh chambers having the same electrode spacing made from film electrodes. Such elevated operating voltages have an advantageous effect on the charge collection behaviour of the ionisation chamber 8, since the drift times are reduced, advantageously so enabling a reduced response/reaction time of the system as a whole. That advantage is especially important for safety reasons, for which a rapid interruption of extraction is required in the event of an error.

Moreover, as a result of the higher mechanical stress and the greater mass of the mesh electrodes in that preferred embodiment, the natural frequency of the ionisation chamber 8 can be shifted to higher frequencies. In ionisation chambers having mesh electrodes of that embodiment, the frequency is about 500 Hz. That high frequency is substantially more favourable than in ionisation chambers having film electrodes, in which even the smallest vibrations as a result of loud talking or unavoidable structure-borne noise vibrations from the vacuum pumps can result in sometimes considerable falsification of the measuring signal.

Thus, as a result of the mesh electrodes of the preferred embodiment of the invention, the microphonic effect that would otherwise cause interference in ionisation chambers 8, 22, 23, 24 is avoided.

A further advantage of the mesh electrodes is the gas-permeability of that construction. As a result, the laminar flow of the counting gas through and between the high-voltage and signal planes is considerably improved, which also contributes to long-term stability. In addition to those advantages, the use of metallised polyester meshes rather than solid metal meshes offers the advantage of having less impact on the beam since, owing to the smaller nuclear charge number of the composite material and the lesser mass present in the centre, fewer secondary products or fragments are produced as the ion beam passes through the mesh and also the angular scatter is less, which reduces the amount of radiation to which healthy tissue is subjected in tumour irradiation or tumour therapy.

Owing to the high melting point and the excellent adhesion of nickel metallisation, the nickel-coated mesh also has the advantage of greater operating safety since damage caused by any sparks has less effect than in the case of an aluminium coating. Thus, the good chemical resistance of the nickel coating also reduces the aging effects as a result of cracked counting gases, which occur when gaseous discharges are triggered. The chemical resistance of the nickel or nickel coating thus contributes to an increase in the length of use or service life of the mesh electrodes used and thus to an increase in the service life of the ionisation chamber.

The screen print mesh used in that embodiment is extremely inexpensive compared with metal meshes, for example made of titanium. Also, screen print meshes have a uniform quality, which also constitutes a great advantage for the manufacture of ionisation chambers 8, 22, 23, 24.

FIG. 5 is a cross-section through the basic structure of an ionisation chamber system 30. That ionisation chamber system 30 is composed of three ionisation chambers 22, 23 and 24, which correspond to the ionisation chambers 8 shown in FIGS. 1 and 2, which are positioned one behind the other in the direction of an ion beam 1. With those three ionisation chambers 22, 23 and 24 that are independent of one another, there is provided the redundancy in the beam current measurement that is necessary to ensure safe operation.

The space available at the beam outlet in a radiation room in front of a patient is greatly limited. Accordingly, those ionisation chambers 22, 23, 24 are installed to be slim (each of a depth of 35 mm) in the direction of the beam in a compact construction. The ionisation chamber system 30 is mounted on a side-mounted common base plate (not shown) so that the base plate does not cover the detector surface or the beam inlet window 3 or the beam outlet window 4.

The ionisation chambers 8, 22, 23, 24 can be replaced individually on the common base plate. For alignment with the centre of the beam, the central scratches on the housing frame 11 in question and on the windows of the ionisation chambers 22, 23, 24 are brought into registration with the system of co-ordinates created by a laboratory system in the medical radiation room. The ionisation chamber system 30 as a whole is positioned on the base plate by means of insulating justifying screws. The precision that can be obtained in this process is ±1 mm.

Arranged on each insulating chamber 8, 22, 23, 24 are adjustment devices, which ensure reproduction of the justification after any development of individual ionisation chambers 22, 23, 24. Each of the ionisation chambers 22, 23 and 24 has brass threaded elements that are attached adhesively at two sites to be conductive and have a transmission resistance of less than 3 $\Omega$. Good earthing of the system as a whole is obtained by means of those brass threaded elements.

The supply of high voltage to the symmetrically arranged high-voltage cathodes 7 is supplied to the high-voltage cathodes 7, which are arranged as cathode plates 10 symmetrically with the counting anode 9 of the active ionisation chamber volume 12, by way of corresponding high-voltage feed-throughs 32 in the housing frame 11. Monitoring of the high voltage by the sensor element 39, described hereinafter, also includes detection of a break in a cable inside the chamber by measuring the volume resistance between the connections 11 and the voltage divider (not shown) at the plane 10. The high voltage is stabilised by a filter device 31 having buffer capacitors 33, 34, as shown in FIGS. 1, 2 and 5, the filter device 31 being arranged in the ionisation chamber 8, 22, 23, 24. By means of that filter device 31 in the ionisation chamber 8, 22, 23, 24, signal variations and falsifications of the measurement values caused by varying operating voltages at high measuring currents are advantageously avoided.

The initial resistance of the high-voltage supply is typically 10 M$\Omega$. The time constant of the combination of high-voltage apparatus and cable plus ionisation chamber is in the order of magnitude of 1 ms, which is substantially longer than the typical time constant of the extraction substructure of, for example, a synchrotron, which is a few 100 $\mu$s. About $10^{-8}$ As occur as collected charge in 1 ms. At a maximum voltage drop below 1 V at the buffer capacitors 33, 34, a capacity of 10 nF is sufficient. In the preferred embodiments of FIGS. 1, 2 and 5, high-voltage capacitors of 50 nF are arranged as buffer capacitors 33, 34. In addition, the ionisation chamber 8, 22, 23, 24 of the embodiment according to FIGS. 1, 2 and 5 has in the chamber volume 5 a T-filter 35, which consists of two resistors 36, 37 each of 1 M$\Omega$ and a capacitor 38 of, for example, 1.2 nF. That T-filter 35 has the advantage of keeping hum interference away from the high-voltage electrodes by filtering.

In order to measure and monitor the high voltage, the high voltage is obtained in the embodiment according to FIGS. 1, 2 and 5 by way of a high-voltage-resistant voltage divider having a fixed dividing ratio (for example 1:1000). Measurement of the operating voltage is effected directly at the high-voltage cathode 7 by means of a high-voltage sensor 39. Monitoring of the high voltage by means of the sensor 39 is preferably used to monitor the charge collection efficiency of the ionisation chamber 8, 22, 23, 24 since the recorded beam particle number is dependent upon the size of the operating voltage.

In the embodiments according to FIGS. 1, 2 and 5, the ionisation chamber 8, 22, 23, 24 has a special gas supply with counting gas of uniform quality and composition. Compared with air-filling, which because of the air humidity influences the sensitivity of an ionisation chamber and reduces the reproducibility of the measurements, a dry gas mixture is used as counting gas in this case. In the embodiment according to FIGS. 1, 2 and 5, there is used as counting gas or chamber gas an argon or krypton/$CO_2$ mixture of 80/20%. That gas mixture has the advantage of having a sufficient W value as counting gas. The W value of that gas mixture is sufficiently low to obtain adequate signals when particle rates are low (for example a minimum of $10^6$ particles per second) and for a good signal/noise ratio and is also sufficiently high to cover a relatively large dynamic range in the particle rates (e.g. factor 100, that is to say a maximum of $10^8$ particles per second).

The chamber volume 5 is hermetically sealed off from the environment so that the counting gas can be kept pure because of the sensitivity of the signal to contamination. Accordingly, even when the chamber is not in operation, an exchange of gas as a result of diffusion with the environment cannot take place or can take place only to a minimal extent. The hermetic sealing of the chamber volume 5 is achieved by means of O-ring seals 19 of the beam inlet window 3 and of the beam outlet window 4 relative to the housing frame 11.

Moreover, there are provided in the housing frame 11 self-closing gas ducts, which are such as not to be confusable with one another, in the counting gas inlet openings 13 and counting gas outlet openings 14 as well as gas-impermeable electrical feed-throughs 32 and feed-throughs 45 for the sensors incorporated in the housing frame 11. The window films 40 of the beam inlet window 3 and the beam outlet window 4 are fixed gas-impermeably by adhesion in the frames 18 of the windows. Materials that do not releases gases are used for all the structural elements used in the chamber volume 5.

The counting gas inlet opening 13 is arranged, with respect to gravity, at the bottom and the counting gas outlet opening 14 is accordingly arranged at the top. Moreover, the ionisation chambers 8, 22, 23, 24 have tubes with holes of different diameter so that, with the co-operation of those holes in the arrangement of the counting gas inlet opening 13 and the counting gas outlet opening 14, a laminar flow can be achieved between the detector planes. A sufficient laminar flow of counting gas of more than two litres per hour through the ionisation chambers has the advantage of achieving reproducible measurement values that are stable in the long term. Since the density of the gas mixture used is higher than that of normal air, the special arrangement of the counting gas inlet opening 13 and the counting gas outlet opening 14 is also of importance in obtaining a laminar flow, since air cushions that it would otherwise not be possible to remove would hinder a laminar flow and would reduce the purity of the counting gas.

In order to make it more difficult for the counting gas to be contaminated by the penetration of extraneous gases, the ionisation chambers 8, 22, 23, 24 are operated at a slightly elevated pressure relative to the ambient air. The extent of the gas reflux from the ionisation chambers 8, 22, 23, 24 is monitored by a sensor in the outlet so that any leaks can be detected.

In the ionisation chamber 8, 22, 23, 24, sensors for gas pressure 15 and for the gas temperature 16 are built into the chamber volume 5. From those measurement values it is possible to determine directly the gas density, which is in turn used in the determination of the value of the beam particle number. By means of the sensor for the gas pressure 15 and the sensor for the temperature 16 it is thus possible to monitor the filling of the ionisation chamber 8, 22, 23, 24 with counting gas and to keep it constant or to take it into account in computer calculations during evaluation.

What is claimed:

1. An ionisation chamber for ion beams (1) having a chamber housing (2), a beam inlet window (3), a chamber volume (5) filled with counting gas, a high-voltage anode (6) and a high-voltage cathode (7) wherein:
   the ionisation chamber (8) is constructed sandwich-like, from flat large-surface-area structures of the above-mentioned components, which are aligned orthogonally relative to the axis of the ion beam, wherein a centrally arranged large-surface-area orthogonally aligned flat counting anode (9) is surrounded on both sides by a large-surface-area flat high-voltage cathode (7) comprising two parallel cathode surfaces (10), and the chamber housing (2) comprises a housing frame (11) which frames a virtually square ionisation chamber volume (12);
   wherein a beam inlet window (3) and a beam outlet window (4) are mounted gas-impermeably and electrically conductively on the housing frame (11) in orthogonal alignment with the ion beam (1), the beam inlet window (3) and the beam outlet window (4) being metallised on the side facing the ionisation chamber volume (12) and the counting anode (9) and the high-voltage cathode (7) consisting of mesh comprising metal-coated plastics fibres and being mounted in frames (20) which are supported against the housing frame (11) in an electrically insulated manner, with electrically insulating spacing elements (21) defining the spacing between the counting anode (9) and the high-voltage cathode (7).

2. The ionisation chamber according to claim 1, wherein the counting gas consists of a gas mixture of argon or krypton and carbon dioxide, preferably in a gas chamber volume mixing ratio of 4:1.

3. The ionisation chamber according to claim 1, wherein the housing frame (11) has a self-sealing counting gas inlet opening (13) and a self-sealing counting gas outlet opening (14).

4. The ionisation chamber according to claim 1, wherein the ionisation chamber (8) has sensors (15, 16) for the counting gas pressure (15) or the counting gas temperature (16) or the high voltage (3 9), which sensors are mounted in the housing frame (11) in gas-impermeably sealed openings (17).

5. The ionisation chamber according to claim 1, wherein the beam inlet window (3) and the beam outlet window (4) comprises radiation-resistant non-polarised plastics films, which are secured to metal plate-shaped frames X18) which in turn seal off the ionisation chamber volume gas-impermeably from the beam inlet window (3) and from the beam outlet window (4) by means of O-ring seals (19) in the housing frame (11).

6. The ionisation chamber according to claim 1, wherein the beam inlet window (3) and the beam outlet window (4) comprise polyimide or polyester films.

7. The ionisation chamber according to claim 1, wherein the beam inlet window (3) and the beam outlet window (4) are aluminised or nickel-plated on the side facing the ionisation chamber volume (12).

8. The ionisation chamber according to claim 1, wherein the counting anode (9) and the high-voltage cathode (7) comprises nickel-coated plastics mesh, preferably nickel-coated polyester mesh.

9. The ionisation chamber according to claim 1, wherein by way of openings (13, 14) in the housing frame, the counting gas can be supplied into the region of the ionisation chamber volume that is lowermost with respect to gravity and can be discharged in the uppermost region.

10. The ionisation chamber according to claim 1, wherein a gas flow sensor for monitoring the throughflow of counting gas is arranged outside the ionisation chamber volume (12).

11. The ionisation chamber according to claim 1, wherein the ionisation chamber (1) can be operated, with a spacing of 5 mm between the high-voltage cathode (7) and the central counting anode (9), at a high voltage of more than 1500 V because of the spacing between the high-voltage cathode (7) and the central counting anode (9) and the composition of the counting gas of an argon/carbon dioxide or krypton/carbon dioxide mixture in a ratio of 80.20%.

12. The ionisation chamber system for ion beams comprising of a plurality of ionisation chambers (22, 23, 24) of the type according to claim 1, wherein the system is used to monitor the intensity of a heavy ion beam, with at least two ionisation chambers (22, 24) being arranged in tandem behind one another in the direction of the ion beam in order to monitor the individual dose of a volume element and the layer dose of a scanned layer, and to monitor the total dose of a treatment cycle independently of the ionisation chamber for monitoring the individual dose and the layer dose.

13. A method of monitoring the intensity of a heavy ion beam by means of ionisation chambers according to the following method steps:
   a) measurement of the intensity dose of an irradiation volume element of a planned irradiation raster for an irradiation layer by means of a first ionisation chamber (22);
   b) monitoring of the measured value of the intensity dose of an irradiation volume element by a second ionisation chamber (23) arranged in tandem behind the first ionisation chamber;
   c) comparison of the measured value of the first ionisation chamber with the monitoring value of the second ionisation chamber and clearance for the irradiation of the next irradiation volume element of a planned irradiation raster of an irradiation layer when the two irradiation intensity values match within a predetermined desired value range;

d) emergency switch-off of the radiation treatment when the predetermined desired value range is exceeded and readjustment of the intensity when it falls short of the predetermined desired value range;

e) repetition of the steps for the subsequent planned irradiation layers until the target volume to be irradiated has been fully scanned; and f) integration of all the measured radiation doses of the monitoring values in a third ionisation chamber (24), which is arranged in tandem behind the first and second ionisation chambers, in order to monitor the total radiation to which a target volume is subjected during a treatment cycle.

14. The method according to claim 13, wherein the order in which the method steps are carried out is adapted optimally to the planned irradiation cycle in question.

15. The method according to claim 13, wherein the monitoring function of the first ionisation chamber (22) and of the second ionisation chamber (23) is provided by a single ionisation chamber.

16. The method according to claim 13, wherein the method is used to monitor ion intensities for ion beams.

* * * * *